United States Patent

Toja et al.

[11] Patent Number: 5,204,479
[45] Date of Patent: Apr. 20, 1993

[54] DERIVATIVES OF 1,2,5,6-TETRAHYDROPYRIDIN-3-CARBOXALDEHYDE OXIME

[75] Inventors: Emilio Toja, Milan; Carla Bonetti, Fontanella; Fernando Barzaghi; Giulio Galliani, both of Monza, all of Italy

[73] Assignee: Roussel Uclaf, Paris, France

[21] Appl. No.: 699,631

[22] Filed: May 15, 1991

[30] Foreign Application Priority Data

May 15, 1990 [IT] Italy .................. 20311 A/90

[51] Int. Cl.$^5$ .................. C07D 211/70
[52] U.S. Cl. .................. 546/328; 514/354
[58] Field of Search .................. 546/328; 514/354

[56] References Cited

U.S. PATENT DOCUMENTS

| | | | |
|---|---|---|---|
| 3,004,979 | 10/1961 | Druey et al. | 546/338 |
| 4,408,054 | 10/1983 | Strupczewski et al. | 546/226 |
| 4,533,675 | 8/1985 | Brossi et al. | 560/28 |
| 4,710,508 | 12/1987 | Bergmeier et al. | 514/357 |
| 4,786,648 | 11/1988 | Bergmeier et al. | 546/338 |
| 4,902,699 | 2/1990 | Toja et al. | 546/338 |
| 4,921,868 | 5/1990 | Galliani et al. | 514/354 |

FOREIGN PATENT DOCUMENTS

| | | |
|---|---|---|
| 725633 | 1/1966 | Canada. |
| 0239445 | 9/1987 | European Pat. Off. . |
| 1258847 | 3/1961 | France. |

OTHER PUBLICATIONS

Chemical Abstracts, vol. 92, No. 13, 31 Mar. 1980-p. 641, 110798y.
Chemical Abstracts, vol. 85 5172X.
Wagner & Zook—Synthetic Organic Chemistry. John Wiley & Sons—p. 646-647.
Chemical Abstracts, CA. 25932p vol. 81, 1974.
March "Advanced Organic Chemistry", 3rd Edition (1985) p. 3 691-700 and 805-806.
Jaffe'—Journal of the American Chemical Society, vol. 76, No. 13, Jul. 5, 1954, pp. 3527-3531.

*Primary Examiner*—Jane T. Fan
*Attorney, Agent, or Firm*—Stevens, Davis, Miller & Mosher

[57] ABSTRACT

The subject of the invention is the compounds of formula (I):

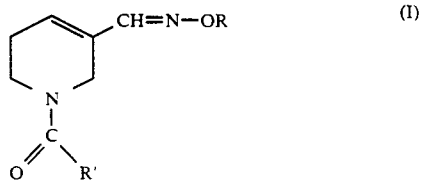

in which:

R represents a hydrogen atom, a saturated or unsaturated, linear, branched or cyclic alkyl radical containing up to 8 carbon atoms, R' represents an amine-containing moiety of an α-amino acid or a peptide, containing as an end group an amine-containing moiety of an α-amino acid as well as their addition salts with organic or mineral acids.

The compounds of formula (I) have useful pharmacological properties which justify their use in therapeutics.

5 Claims, No Drawings

DERIVATIVES OF 1,2,5,6-TETRAHYDROPYRIDIN-3-CARBOXALDEHYDE OXIME

The present invention relates to new derivatives of 1,2,5,6-tetrahydropyridin-3-carboxaldehyde oxime, their preparation process and their use as medicaments.

A subject of the invention is the compounds of formula (I):

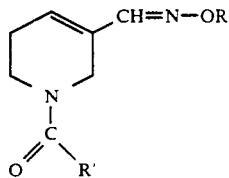

in which:
R represents a hydrogen atom, a saturated or unsaturated, linear, branched or cyclic alkyl, alkenyl or alkynyl radical containing up to 8 carbon atoms,
R' represents the amine-containing moiety preferably of an α-amino acid or a peptide containing as an end group an amine-containing moiety of an α-amino acid, as well as their pharmaceutically acceptable acid addition salts.

Among the addition salts with acids, there can be mentioned those formed with mineral acids, such as the following acids: hydrochloric, hydrobromic, sulfuric or phosphoric, or with organic acids such as the following acids: formic, acetic, propionic, benzoic, maleic, fumaric, succinic, tartaric, citric, oxalic, glyoxylic, aspartic, alkanesulphonic, such as methane- or ethanesulphonic, arylsulphonic such as benzene- or paratoluenesulphonic.

When R represents a saturated, linear or branched alkyl radical, it is preferably a methyl, ethyl, n-propyl, isopropyl, n-butyl, isobutyl, n-pentyl, tert-butyl, tert-pentyl, neopentyl or n-hexyl.

When R represents an unsaturated alkenyl or alkynyl radical, it is preferably an ethylenic radical such as, for example, a vinyl, allyl, 1,1-dimethylallyl or 2-butenyl radical, or an acetylenic radical such as, for example, an ethynyl or propynyl radical.

When R represents a cyclic alkyl radical, it is preferably a cyclopropyl, cyclobutyl, cyclopentyl, cyclohexyl, cyclopropylmethyl, cyclobutylmethyl, cyclopentylmethyl or cyclohexylmethyl radical.

In general formula (I) and in what follows, the amino acid is preferably an alpha-amino acid and can be chosen from the group constituted by Ala, Val, Ival, Leu, Ile, Asp, Asn, Glu, Gln, Ser, Thr, Cys, Met, Lys, Arg, Phe, Tyr, Trp, His and Pro, Nva, Nle, Hyp, Orn, these acids being in D or L form, as well as by Sar and Gly; in the case of a peptide containing 2, 3 or 4 amino acids, these are chosen from the group constituted by the above amino acids.

It is accepted by convention that the symbols of alpha-amino carboxylic acids represent these acids in their D or L configuration or by a mixture of D and L, (for example, the term Ala signifies Alanine in D form or L form, or in the form of a D and L mixture).

A more particular subject of the invention is:
the compounds of formula (I) in which R represents a saturated or unsaturated linear alkyl radical containing up to 4 carbon atoms,
the compounds of formula (I) in which R represents a methyl radical,
the compounds of formula (I) in which R' represents the amine-containing moiety of an α-amino carboxylic acid of L configuration,
the compounds of formula (I) in which R' represents,

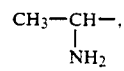

which is the amine-containing moiety of the α-amino acid alanine,
the compounds of formula (I) in which R' represents the amine-containing moiety of an amino acid containing two acid functions, for example, R' may be the amine-containing moiety of aspartic acid (i.e.,

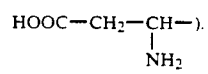

As is evident from the above an amine-containing moiety of an α-amino acid is a remnant of an α-amino acid and does not contain the carboxyl function normally adjacent to the carbon atom α to the carboxyl.

Among these compounds, there can be cited the compounds presented in the form of the compound of formula (X):

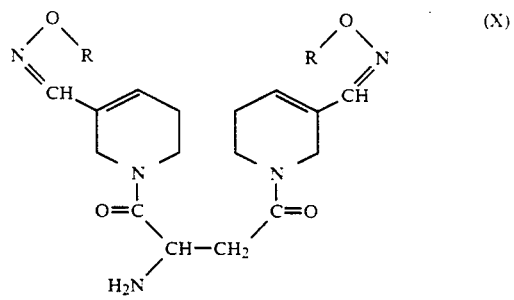

in which R keeps its previous meaning, as well as their addition salts with organic or mineral acids.

A quite special subject of the invention is the compound of formula (I) of which the preparation is given hereafter in the experimental part.

The products of the invention show very useful pharmacological properties, notably a cholinomimetic activity by oral route and which have a long-lasting action.

The products also show a good dissociation between central activity and peripheral activity.

It is well known that learning and memory disorders in old people are especially related to a deficit of the central cholinergic system, in particular in senile dementia and Alzheimer's disease.

It is therefore evident that products having a central cholinergic action can be used in the therapeutic treatment of these illnesses (Bartus, R. I. Science 217, 408, 1982).

It has been demonstrated that arecoline injected by intravenous route has a positive effect on patients having a memory deficit (Sitaram N. et al. Science 201, 274, 1978) (Christie J. E. et al. Brit. J. Psychiatry 138, 46, 1981).

A limitation of the therapeutic use of arecoline is linked to the fact that this product has a very weak activity by oral route and a short-lasting action.

The products which are a subject of the invention showed, after administration by oral route, a central cholinomimetic activity greater than that of arecoline and with a longer-lasting action.

Therefore a subject of the invention is the products of the invention as medicaments useful notably in the treatment of Alzheimer's disease or senile dementia and also in the treatment of memory disorders.

The usual dose is variable according to the affection in question, the patient treated and the administration route; it can be comprised between 10 mg and 300 mg/day, or between 50 and 200 mg/day, and for example, between 15 and 150 mg/day in one or more doses for the product of Example 1 administered by oral route.

Also a subject of the present invention is the pharmaceutical compositions containing as active ingredient at least one product of formula (I).

The pharmaceutical compositions according to the invention can be solid or liquid and can be presented in the pharmaceutical forms currently used in human medicine, such as for example, plain or sugar-coated tablets, capsules, granules, suppositories, injectable preparations; they are prepared according to the usual methods.

The active ingredient or ingredients can be incorporated with the excipients usually employed in such pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, and preservatives.

Also a subject of the invention is a process for the preparation of compounds of formula (I) characterized in that an acid of formula (II):

in which R" represents the amine-containing moiety of an amino acid R'CO$_2$H in which the amine group is blocked and the carboxylic function has been activated, is subjected to reaction with the compound of formula (III):

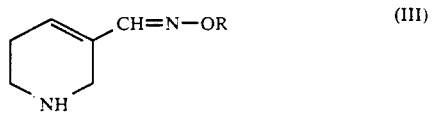

in which R is defined above, in order to obtain the compound of formula (I'):

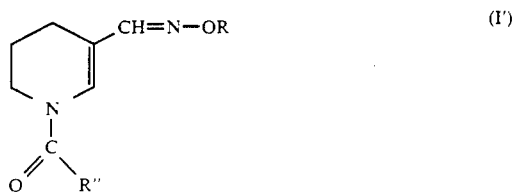

then the compound of formula (I') is subjected to the action of a release agent of the amine blocking function in order to obtain the compound of formula (I):

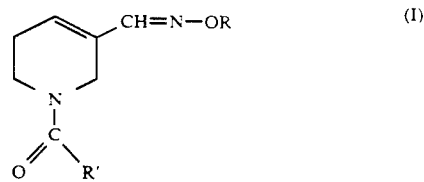

wherein R' and R are defined above, which is subjected, if desired, to the action of a pharmaceutically acceptable acid in order to form the pharmaceutical acceptable salt.

In a preferred embodiment of the process of the invention:

A—the amine function or functions are protected by easily labile groups currently used in pharmaceutical chemistry, for example the groups:

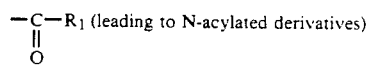

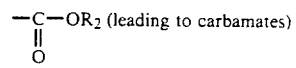

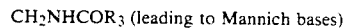

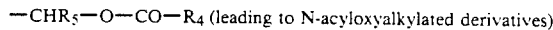

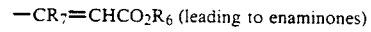

the radicals $R_1$, $R_2$, $R_3$, $R_4$, $R_5$, $R_6$ and $R_7$ representing hydrocarbon radicals.

A preferred group for blocking the amine function is 9-fluorenyl methyloxy carbonyl (FMOC). Numerous FMOC L amino acids are also commercially available, for example FMOC-L-alanine.

There can also be used as a preferred protector group, the group:

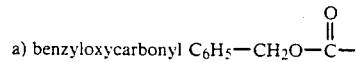

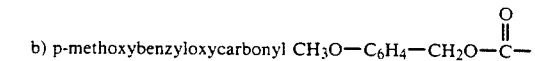

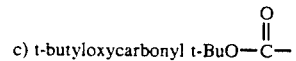

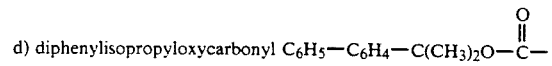

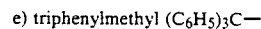

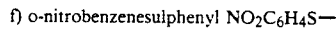

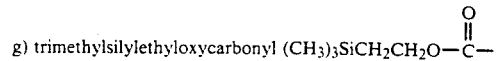

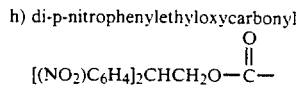

B—To activate the carboxyl function, the acid can be converted into the acid halide, for example into acid chloride, using thionyl chloride in an inert solvent such as methylene chloride or chloroform. The amino acid can also be converted into other derivatives, for example:
—into an azide

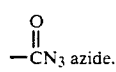
   azide.

—into a mixed anhydride,
—into esters, for example into p-nitro phenyl ester, polyhalogeno phenyl esters, 1-hydroxy benzotriazole esters, or also esters of N-hydroxy succinimide, 1-hydroxy benzotriazole, 2-hydroxy pyridine or 2-mercapto pyridine.

C—The reaction of the compound of formula (II) with the compound of formula (III) takes place in an inert solvent such as methylene chloride, chloroform, dichloroethane, benzene, toluene, optionally in the presence of a base such as TEA (triethylamine), DABCO (triethylene diamine), DBN (1,5-diazabicyclo [4,3,0] non-5-ene), DBU (1,8-diazabicyclo [5,4,0] undec-7-ene).

D—The reaction to release the protected amine function by the FMOC group takes place using a secondary amine such as diethylamine, piperidine or morpholine, and operating at ambient temperature.

The protected amine function can also be released by other groups by means of hydrogenolysis, acid hydrolysis or using tetrabutylammonium fluoride $Bu_4NF$.

E—The formation of salts is carried out by the addition of acids in the standard manner.

The compounds of formula (III) used as starting products are known products, described and claimed in European Patent Application 239,445.

A more particular subject of the invention is a process, characterized in that a compound of formula ($II_A$):

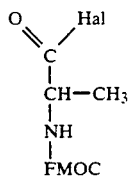

in which Hal represents a halogen atom and FMOC represents a fluorenylmethoxycarbonyl radical, is subjected to the action of a compound of formula (III):

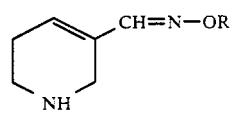

in order to obtain the compound of formula (IV):

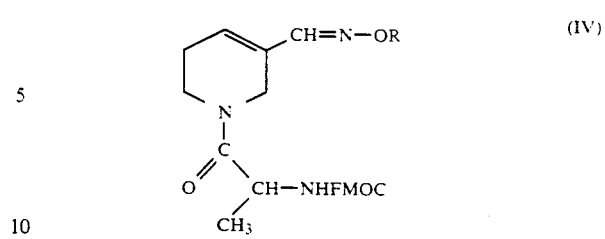

the amine function of which is released in order to obtain the corresponding compound of formula ($I_A$):

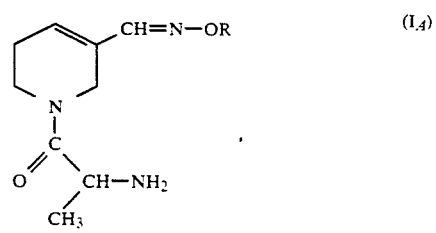

In a preferred embodiment:
—Hal is a chlorine atom,
—the condensation reaction of the compound of formula ($II_A$) and of formula (III) is carried out in dichloroethane in the presence of a base such as DBU, DBN or TEA.
—the reaction to release the amine function takes place via the action of a base such as morpholine, at ambient temperature.

The following examples illustrate the invention without however limiting it.

EXAMPLE 1

(L)-2-amino-1-[(3-(methoxyimino)-methyl)-1,2,5,6-tetrahydro-1-pyridinyl]-1-propanone STAGE A:
N-[2-[3-((methoxyimino)-methyl)-1,2,5,6-tetrahydro-1-pyridinyl]-1-methyl-2-oxoethyl]-carbamate of 9-fluorenylmethyl.

4.6 g of 2-(9-fluorenyl-methoxycarbonylamino) L-propanoyl chloride is dissolved in 50 cm³ of dichloromethane, a solution containing 1.78 g of 1,2,5,6-tetrahydro-3-pyridine carboxaldehyde O-methyloxime and 1.99 g of 1,8-diazabicyclo-[5,4,0]-undec-7-ene in 40 cm³ of dichloromethane is added slowly. After agitation for one hour at ambient temperature, evaporation takes place under reduced pressure, the mixture is taken up in water and extracted with ethyl acetate. The solvents are dried and evaporated off. After chromatography on silica (eluant: ethyl acetatehexane 1-1), 3.92 g of an oil is obtained which solidifies under reduced pressure.

STAGE B (L-)
2-amino-1-[(3-(methoxyimino)-methyl)-1,2,5,6-tetrahydro-1-pyridinyl]-1-propanone 3.8 g of N-[2-[3-((methoxyimino)-methyl)-1,2,5,6-tetrahydro-1-pyridinyl]-1-methyl-2-oxoethyl]carbamate of 9-fluorenylmethyl prepared in Stage A and 50 cm³ of morpholine are agitated for 40 minutes at ambient temperature. Most of the morpholine is eliminated under reduced pressure, the remaining mixture is poured into 350 cm³ of cold water and the N-9-fluorenylmethylmorpholine is eliminated by filtration. The filtrate is concentrated to a volume of about 200 cm³, extracted several times with dichloromethane, dried and the solvent is evaporated off. The residue is left under reduced pressure for 24 hours, chromatographed on silica (eluant: chloroform—methanol 7-3) and 1.8 g of an oily product is obtained which is salified by the addition of 4 3 cm³ of 2N hydrochloric ethanol. After crystallization from ethanol and ether, 1.87 g of expected product is obtained.

M.p. = 215°–217° C. (decomp.).

Analysis: $C_{10}H_{17}N_3O_2$, HCl: 247.726 Calculated: C% 48.49 H% 7.32 N% 16.96 Found: 48.51 7.36 16.99

Preparation of 2-(9-fluorenyl-methoxy-carbonylamino)-L-propanoyl chloride used at the start of the example A mixture made up of 5 g of 9-fluoromethoxycarbonyl-(L)-alanine and 9.5 cm³ of thionyl chloride in 60 cm³ of dichloromethane is heated under reflux for 20 minutes. The solvent is eliminated, the residue is taken up in a small amount of dichloromethane, precipitation is carried out using hexane and 4.83 g of expected product is obtained.

M.p. = 108°–110° C.

PHARMACOLOGICAL STUDY

Acute toxicity

The test is carried out on male mice ($CD_1$ Charles Rivers) weighing 22 to 24 g, which have gone without food for 16 hours. The products are administered by oral route at a dose of 1000, 500, 250 and 125 mg/kg. The mortality is noted for 7 days after the treatment.

Test on the isolated ileum of the guinea-pig

Ileum fragments are removed from guinea-pigs killed by decapitation. The isolated ileum is placed in 10 cm³ of Tyrode solution at 37° C. and aerated with a mixture of oxygen (95%) and carbon dioxide (5%). The contractions caused by the products are recorded using a sensor connected to a polygraph. The test products are added, at concentrations of between $1.10^{-3}M$ and $1.10^{-8}M/l$.

The products showing a contracting effect are tested vis-a-vis atropine and hexamethonium to establish if the activity is of "muscarinic" or "nicotinic" type.

The possible antagonist activity of the products is tested vis-a-vis acetylcholine.

The agonist activity is expressed in $pD_2$ (negative logarithm of the dose which produces 50% of the maximum effect).

The antagonist activity is expressed in $DE_{50}$ (dose reducing by 50% the maximum response induced by acetylcholine).

Diarrheic activity

The test is carried out on male mice ($CD_1$ Charles Rivers) weighing 25 to 30 g, which have gone without food for 6 hours. The product dissolved at 5% in methocel is administered by oral route, using a probang.

The control animals receive only the excipient.

After treatment, the animals are put separately into cages of which the bottom is covered with blotting paper and they are observed for 30, 60, 120 and 180 minutes.

The absorbent sheets of paper are changed after each observation.

The consistency of the faeces is evaluated according to the method of Randall and Baruth (Arch. Int. Pharmacodyn. 220, 94, 1976) using the following scale of values:

0: firm consistency,
1: slightly soft faeces with or without moist ring,
2: slightly soft faeces with presence of a well-defined moist circle,
3: soft faeces with presence of a large moist circle,
4: faeces without consistency with presence of a very large moist circle.

For each product, the dose was noted which causes diarrhoea in 50% of the animals according to the method of Miller and Tainter (Proc. Soc. Exp. Biol. Med., 57, 261, 1944).

Hypothermic activity

The test is carried out on male mice ($CD_1$ Charles Rivers) weighing 25 to 30 g, which have gone without food for 6 hours.

The body temperature is noted using a thermocouple placed about 1.5 cm³ inside the rectum and connected to an electrical temperature recorder.

The products are administered by oral or sub-cutaneous route and the temperatures are noted at 0 and 30 minutes, one hour, 2 hours and 3 hours after treatment.

The degree of hypothermia is evaluated as the difference between the treated animals and the controls and the dose necessary to reduce the body temperature by 1° C. is determined.

The duration of the action of the products is determined using doses which can reduce the temperature by 1° C. to 1.5° C.

The results obtained during the biological tests have shown that administered by oral route, the product of Example 1 has an important cholinomimetic activity and a long-lasting action, the product of Example 1 also has an important dissociation between central activity and peripheral activity.

We claim:

1. A compound of formula (I):

in which:

R represents hydrogen, alkyl, alkenyl, alkynyl or aralkyl containing up to 8 carbon atoms, and R' represents a member selected from the group consisting of $$CH_3-CH-,\ CH_3-CH-CH-,\ CH_3-CH_2-\underset{CH_3}{\underset{|}{\overset{NH_2}{\overset{|}{C}}}},$$
$$\underset{NH_2}{|}\ \ \ \ \underset{CH_3\ NH_2}{|\ \ \ |}$$

$$CH_3-CH-CH_2-CH-,\ \text{and}\ CH_3CH_2CH-CH-$$
$$\underset{CH_3}{|}\ \ \ \underset{NH_2}{|}\ \ \ \ \ \ \ \ \ \underset{CH_3\ NH_2}{|\ \ \ |}$$

or a pharmaceutically acceptable addition salt thereof.

2. The compound of formula (I) as defined in claim 1, in which R represents alkyl containing up to 4 carbon atoms, or a pharmaceutically acceptable addition salt thereof.

3. The compound of formula (I) as defined in claim 2, in which R represents methyl, or a pharmaceutically acceptable addition salt thereof.

4. The compound of formula (I) as defined in claim 1, in which R' represents

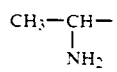

or a pharmaceutically acceptable addition salt thereof.

5. The compound: (L-) 2-amino-1-[(3-(methoxyimino)-methyl)-1,2,5,6-tetrahydro-1-pyridinyl]-1-propanone.

* * * * *